US00PP37210P2

(12) United States Plant Patent
Gomes da Costa

(10) Patent No.: US PP37,210 P2
(45) Date of Patent: Jan. 13, 2026

(54) ***MANDEVILLA* PLANT NAMED 'TVMD847'**

(50) Latin Name: *Mandevilla sanderi*
Varietal Denomination: TVMD847

(71) Applicant: NICOLAAS JOSEF SCHOENMAKER e OUTROS, Sao Paulo (BR)

(72) Inventor: Everton Gomes da Costa, Sao Paulo (BR)

(73) Assignee: NICOLAAS JOSEF SCHOENMAKER e OUTROS, Sao Paulo (BR)

( * ) Notice: Subject to any disclaimer, the term of this patent is extended or adjusted under 35 U.S.C. 154(b) by 0 days.

(21) Appl. No.: 18/808,021

(22) Filed: Aug. 18, 2024

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Mandevilla* plant named 'TVMD847', characterized by its upright to somewhat outwardly spreading plant habit; early and freely flowering habit; and deep red-colored flowers.

1 Drawing Sheet

Botanical designation: *Mandevilla sanderi.*
Cultivar denomination: 'TVMD847'.

BACKGROUND OF THE INVENTION

The present invention relates to a new and distinct cultivar of *Mandevilla* plant, botanically known as *Mandevilla sanderi*, and hereinafter referred to by the name 'TVMD847'.

The new *Mandevilla* plant is a product of a planned breeding program conducted by the Inventor in Sao Paulo, Brazil. The objective of the breeding program is to develop new compact and freely flowering *Mandevilla* plants with large flowers that resist fading and perform well in the garden.

The new *Mandevilla* plant originated from a cross-pollination in September 2017 in Sao Paulo, Brazil of a proprietary breeding selection of *Mandevilla sanderi* identified as code name TVMD196, not patented, as the female, or seed, parent with a proprietary breeding selection of *Mandevilla sanderi* identified as code name TVMD301, not patented, as the male, or pollen, parent. The new *Mandevilla* plant was discovered and selected by the Inventor as a single flowering plant from within the progeny of the stated cross-pollination grown in a controlled greenhouse environment in Sao Paulo, Brazil in July 2019.

Asexual reproduction of the new *Mandevilla* plant by terminal stem cuttings in a controlled environment in Sao Paulo, Brazil since December 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices.

The phenotype may vary somewhat with variations in environmental conditions such as temperature and light intensity, without, however, any variance in genotype.

The following traits have been repeatedly observed and are determined to be the unique characteristics of 'TVMD847'. These characteristics in combination distinguish 'TVMD847' as a new and distinct *Mandevilla* plant:

1. Upright to somewhat outwardly spreading plant habit.
2. Early and freely flowering habit.
3. Deep red-colored flowers.

Plants of the new *Mandevilla* can be compared to plants of the female parent selection. Plants of the new *Mandevilla* differ primarily from plants of the female parent selection in the following characteristics:

1. Flowers of plants of the new *Mandevilla* are darker red in color than flowers of plants of the female parent selection.
2. Flower throats of plants of the new *Mandevilla* are darker orange in color than flower throats of plants of the female parent selection.

Plants of the new *Mandevilla* can be compared to plants of the male parent selection. Plants of the new *Mandevilla* differ primarily from plants of the male parent selection in the following characteristics:

1. Flowers of plants of the new *Mandevilla* are deep red in color whereas flowers of plants of the male parent selection are dark pink in color.
2. Flower throats of plants of the new *Mandevilla* are darker orange in color than flower throats of plants of the male parent selection.

Plants of the new *Mandevilla* can also be compared to plants of *Mandevilla sanderi* 'TVMD258', disclosed in U.S. Plant Pat. No. 35,329. In side-by-side comparisons, plants of the new *Mandevilla* differ primarily from plants 'TVMD258' in the following characteristics:

1. Flowers of plants of the new *Mandevilla* are longer than flowers of plants of 'TVMD258'.

2. When opening, flowers of plants of the new *Mandevilla* are darker red in color than opening flowers of plants of 'TVMD258'.
3. Flower throats of plants of the new *Mandevilla* are darker orange in color than flower throats of plants of 'TVMD258'.

BRIEF DESCRIPTION OF THE PHOTOGRAPH

The accompanying colored photograph illustrates the overall appearance of the new *Mandevilla* plant showing the colors as true as it is reasonably possible to obtain in colored reproductions of this type. Colors in the photograph may differ slightly from the color values cited in the detailed botanical description which accurately describe the actual colors of the new *Mandevilla* plant.

The photograph is a side perspective view of a typical flowering plant of 'TVMD847' grown in a container.

DETAILED BOTANICAL DESCRIPTION

The aforementioned photograph and following observations, measurements and values describe plants grown in July in 15-cm containers in a polyethylene-covered greenhouse in Sao Paulo, Brazil and under cultural practices typical of commercial *Mandevilla* production. During the production of the plants, day temperatures ranged from 20° C. to 35° C. and night temperatures ranged from 10° C. to 20° C. Plants were pinched three times: four weeks, six weeks and eight weeks after planting. Plants were 33 weeks old when the photograph and description were taken. In the following description, color references are made to The Royal Horticultural Society Colour Chart, 2015 Edition, except where general terms of ordinary dictionary significance are used.

Botanical classification: *Mandevilla sanderi* 'TVMD847'.

Parentage:

*Female, or seed, parent*.—Proprietary selection of *Mandevilla sanderi* identified as code number TVMD196, not patented.

*Male, or pollen, parent*.—Proprietary selection of *Mandevilla sanderi* identified as code number TVMD301, not patented.

Propagation:

*Type*.—By vegetative cuttings.

*Time to initiate roots, summer*.—About three weeks at temperatures about 20° C. to 35° C.

*Time to initiate roots, winter*.—About three weeks at temperatures about 20° C. to 25° C.

*Time to produce a rooted young plant, summer*.—About 20 to 25 days at temperatures about 20° C. to 35° C.

*Time to produce a rooted young plant, winter*.—About 25 to 30 days at temperature about 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Upright to somewhat outwardly plant habit; roughly broadly obovate in overall shape; and moderate to rapid growth rate.

*Plant height, soil level to top of foliar plane*.—About 26 cm.

*Plant height, soil level to top of floral plane*.—About 29 cm.

*Plant diameter* (*spread*).—About 21 cm.

*Lateral branch description*.—Branching habit: Moderate branching habit, typically about two primary lateral branches each with about two secondary lateral branches. Length: About 12 cm. Diameter: About 2.2 mm. Internode length: About 1.5 cm. Aspect: Primary lateral branches, mostly upright; secondary lateral branches, about 30° from primary branch axis. Texture and luster: Smooth, glabrous; semi-glossy; becoming woody with development. Color, developing: Close to 143C. Color, developed: Close to 143C; when woody, close to 177B.

Leaf description:

*Arrangement*.—Opposite, simple.

*Length*.—About 6.4 cm.

*Width*.—About 3.3 cm.

*Shape*.—Obovate to ovate.

*Apex*.—Acuminate.

*Base*.—Rounded.

*Margin*.—Entire; not lobed.

*Texture and luster, upper and lower surfaces*.—Smooth, glabrous; moderately coriaceous; moderately glossy.

*Venation pattern*.—Pinnate.

*Color*.—Developing leaves, upper surface: Close to 146A. Developing leaves, lower surface: Close to 147C. Fully expanded leaves, upper surface: Close to NN137A; venation, close to 144B. Fully expanded leaves, lower surface: Close to 138B; venation, close to 145C.

*Petioles*.—Length: About 1.3 cm. Diameter: About 1.6 mm. Texture and luster, upper and lower surfaces: Smooth, glabrous; slightly glossy. Color, upper surface: Close to 144B. Color, lower surface: Close to 145B.

Flower description:

*Flower type and flowering habit*.—Single salverform flowers arranged in terminal and axillary cymes; flowers face mostly upright to outwardly; freely flowering habit with about two fully open flowers per inflorescence and about 17 flower buds and open flowers develop per plant at one time.

*Natural flowering season*.—Plants flower continuously year-round in Brazil; plants begin flowering about 25 weeks after planting rooted young plants.

*Flower longevity on the plant*.—Individual flowers last about ten days; flowers not persistent.

*Fragrance*.—None detected.

*Inflorescence height*.—About 10 cm.

*Inflorescence diameter*.—About 8 cm.

*Flower buds*.—Length: About 6 cm. Diameter: About 9 mm. Shape: Lanceolate. Texture and luster: Smooth, glabrous; slightly glossy. Color: Distally, close to 183A; mid-section, close to 184C and proximally, close to 145B.

*Flowers*.—Appearance: Flared trumpet, corolla fused and five-parted. Diameter: About 8 cm by 8 cm. Depth (length): About 6.5 cm. Throat diameter: About 1.5 cm. Tube length: About 1.8 cm. Tube diameter: About 3.4 mm.

*Corolla*.—Quantity and arrangement: Five petals arranged in a single whorl; lower 50% portion of the petals are fused into a funnelform tube. Petal length:

About 3.1 cm. Petal width: About 3.2 cm. Petal shape and appearance: Unequal and asymmetric; roughly spatulate; slightly convex. Petal apex: Acute. Petal margin: Entire; not undulate. Petal texture and luster, upper and lower surfaces: Smooth, glabrous; slightly glossy. Throat texture: Smooth, glabrous. Tube texture: Smooth, glabrous. Color: Petal, when opening, upper surface: Close to 59A. Petal, when opening, lower surface: Close to 183A. Petal, fully opened, upper surface: Close to 53A; venation, close to 53A; color does not change with subsequent development. Petal, fully opened, lower surface: Close to 181A; venation, close to 181A; color does not change with subsequent development. Throat: Distally, close to 53A and proximally, close to 169B; venation, close to 53A. Tube: Distally, close to 53D and proximally, close to 150D; venation, close to 53D; at the base, close to 151D.

*Sepals*.—Quantity and arrangement: Five sepals arranged in a single whorl. Length: About 4 mm. Width: About 2 mm. Shape: Lanceolate. Apex: Narrowly acuminate. Base: Broadly cuneate and fused. Margin: Entire. Texture and luster, upper surface: Smooth, glabrous; slightly glossy. Texture and luster, lower surface: Smooth, glabrous; matte. Color: When developing, upper and lower surfaces: Close to 145C. Fully developed, upper and lower surfaces: Close to 145C.

*Peduncles*.—Length: About 2.4 cm. Diameter: About 2.3 mm. Aspect: About 85° from lateral branch axis. Texture and luster: Smooth, glabrous; moderately glossy. Color: Close to 143B.

*Pedicels*.—Length: About 9 mm. Diameter: About 1.8 mm. Aspect: About 85° from peduncle axis. Texture and luster: Smooth, glabrous; moderately glossy. Color: Close to 144B.

*Reproductive organs*.—Stamens: Quantity and arrangement: Typically five; basifixed; anthers connivent. Filament length: About 2 mm. Filament color: Close to 145B. Anther shape: Narrowly sagittate. Anther size: About 4 mm by 8 cm. Anther color: Close to 160B. Pollen color: Close to 155B. Pistils: Quantity: Typically one. Pistil length: About 2.6 cm. Style length: About 2.3 cm. Style color: Close to 145D. Stigma diameter: About 1.6 mm. Stigma shape: Club-shaped, pointed. Stigma color: Close to 145D. Ovary color: Close to 145B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'TVMD847' as herein illustrated and described.

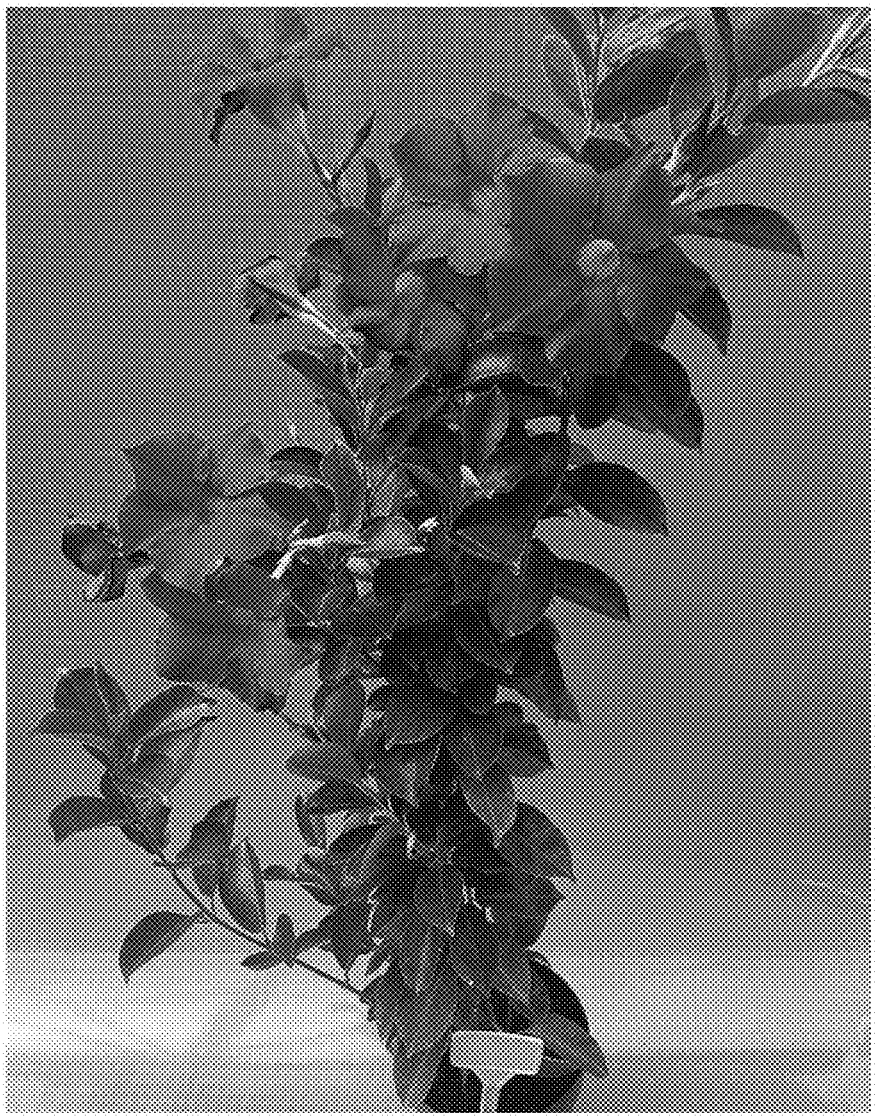

* * * * *